Figure 1:
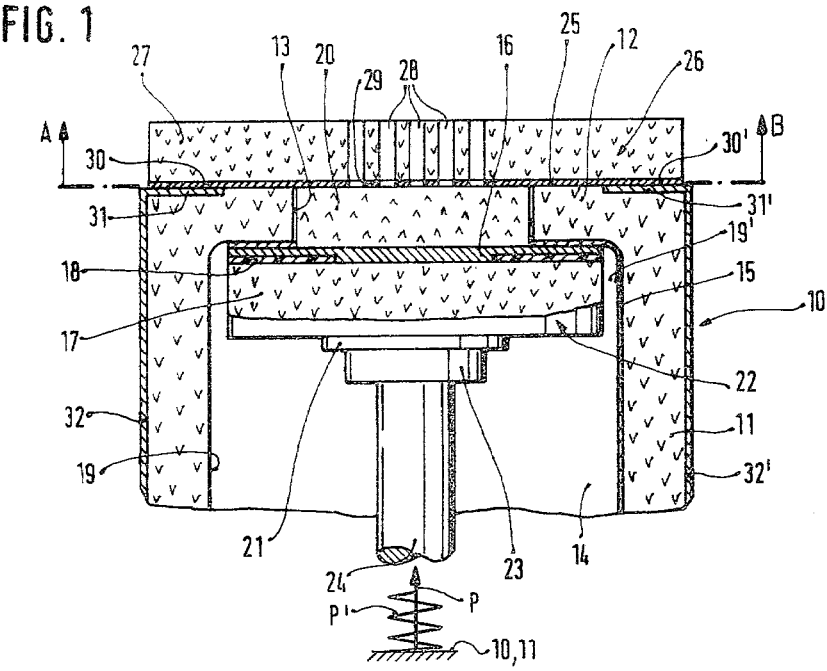

United States Patent [19]

Beyer et al.

[11] 4,305,803
[45] Dec. 15, 1981

[54] GAS SENSOR CONSTRUCTION, PARTICULARLY TO DETERMINE OXYGEN CONTENT COMBUSTION EXHAUST GASES, PARTICULARLY FROM INTERNAL COMBUSTION ENGINES

[75] Inventors: Barbara Beyer, Stuttgart; Hermann Dietz, Gerlingen; Karl Friese, Leonberg, all of Fed. Rep. of Germany

[73] Assignee: Robert Bosch GmbH, Stuttgart, Fed. Rep. of Germany

[21] Appl. No.: 184,085

[22] Filed: Sep. 4, 1980

[30] Foreign Application Priority Data

Sep. 21, 1979 [DE] Fed. Rep. of Germany ....... 2938179

[51] Int. Cl.³ ........................................... G01N 27/58
[52] U.S. Cl. ............................................... 204/195 S
[58] Field of Search ........................... 204/195 S, 1 S

[56] References Cited

U.S. PATENT DOCUMENTS 4,155,827  5/1979  Maurer et al. .................. 204/195 S
4,222,840  9/1980  Murphy et al. ................. 204/195 S

*Primary Examiner*—G. L. Kaplan
*Attorney, Agent, or Firm*—Frishauf, Holtz, Goodman & Woodward

[57] ABSTRACT

To facilitate manufacture of a sensor, particularly a polarographic sensor which has no sealing or heat expansion difficulties and only low heat capacity in the measuring range and electrical connections, a solid electrolyte (17) is formed as a plate extending transversely across a bottom opening (13) of a preferably ceramic tube (11), the plate having two electrodes (16,21) applied to its major sides. The side facing the opening (13) is covered with a ceramic layer (20) having a predetermined diffusion or migration resistance to oxygen molecules. The electrical connections are formed by a conductive track (15) extending on the inside of the ceramic tube, in contact with the sensing electrode on one side of the plate; and a counter head (23) connected to a conductive bolt or pin (24) and resiliently spring pressed against the electrode, and holding the plate (17) and the diffusion barrier (20) thereon in position in the sensor. The test gas is applied to the diffusion resistance layer through a ceramic heat storage plate, for instance, having openings therethrough, which has a film-type heater applied thereto, connected to a current source by conductive tracks (31, 31'; 32, 32') positioned on the outside of the ceramic tube.

8 Claims, 2 Drawing Figures

U.S. Patent    Dec. 15, 1981    4,305,803

GAS SENSOR CONSTRUCTION, PARTICULARLY TO DETERMINE OXYGEN CONTENT COMBUSTION EXHAUST GASES, PARTICULARLY FROM INTERNAL COMBUSTION ENGINES

The present invention relates to a gas sensor, and more particularly to a gas sensor to determine the oxygen content in combustion exhaust gases, especially exhaust gases from internal combustion (IC) engines, typically of the automotive type.

BACKGROUND AND PRIOR ART

Various types of sensors have been proposed, and one type of sensor, to which the present invention is particularly applicable, is a polarographic sensor, in which a bias voltage is connected across electrodes, and the diffusion limiting current. This current is representative of the oxygen content in gases. In one specific type of arrangement—see published German Disclosure Document DE-OS 27 11 880 (to which U.S. appln. Ser. No. 6,093, filed Jan. 24, 1979, Dietz, and now abandoned and refiled as U.S. appln. Ser. No. 213,049 filed Apr. 12, 1980 corresponds), the output current can be arranged to be essentially analagous to the oxygen concentration in the gas to be tested or analyzed. In this sensor, two electrodes are provided, one exposed to the test and the other to a reference gas, typically oxygen in the air. The construction of the sensor itself raises difficulties in sealing the gas diffusion barrier and the side of the electrolyte to which the sensing electrode is applied from the side of the electrolyte on which the reference electrode is applied, exposed to a reference gas. It is also difficult to maintain the seal throughout an extended lifetime due to differences in thermal coefficience of expansion of the components which are adjacent the solid electrolyte ion conductive body, such as a holding tube, diffusion barriers, the solid electrolyte itself, the sensing and reference electrodes and the like. Contacting the sensing electrode and the reference electrode, and associated conductive tracks also causes difficulty due to the high thermal loading in the sensing region. This high thermal loading interferes with operating reliability over an extended period of time.

It has also been proposed—see U.S. Pat. No. 4,155,827, Maurer et al, assigned to the assignee of the present application—to construct a potentiometric sensor, that is a sensor operating analagous to a fuel cell in which a spring loaded pressure contact is used, and heater elements are provided. The construction is rather complex and, when intended to be made under mass production conditions, may unduely increase the cost of the sensor.

THE INVENTION

It is an object to provide a sensor, and more particularly a polarographic type sensor which is simple to make, permits differential expansions under changing temperature conditions and provides a reliable reproducable output over a long period of time.

A gas impervious layer is located on the edge portion of a plate-like oxygen ion conductive solid electrolyte body, one side of which has the electrode applied thereto. The electrode extends over the gas impervious layer. The plate itself is maintained in position within an essentially tubular housing by a central bolt or plug element which passes through the housing and is pressed by a spring or other resilient biasing force towards an in-turned edge portion of the housing which carries the conductor to contact the electrode. The opposite side of the plate likewise has an electrode applied thereto and is contacted by the central bolt, thus also has a spring biased electrical contact terminal. The side remote from the bolt carries a gas diffusion barrier to permit just sufficient oxygen to reach the sensing electrode to be converted by electrochemical reaction into diffusion limited current, as explained fully in the Reference Dietz application Ser. No. 6,093, and DE-OS 27 11 880. Preferably, the plate supported by the bolt has a slightly smaller outer diameter than the inner diameter of a tubular housing to permit expansion of the plate under heating condition, the pressure sliding contact providing for wiping contact action and likewise permitting differential expansion of the solid electrolyte body in the housing which, for example, may be made of ceramic. A heat storage disk formed with openings for the passage of gas therethrough is located at the terminal portion of the housing, protecting the diffusion barrier layer and providing a heat equilization and storage zone, thus preventing excessive temperature gradients and rapid temperature swings. Preferably, a heating element, for example in film form is located beneath the heat storage plate, contacted to electrical conductors which, for example, can be carried on the outside of the tubular sensor.

The sensor has the advantage that sealing problems no longer arise and different expansion of elements due to heating of the various components are compensated. The electrical contacts and connections within the hot region, that is, the sensing zone are reliable in operation. The sensor, additionally, carries a heater element in the sensing region which can be easily made by modern mass production technology, for example, in thin film technology, and is directly secured to the sensor. The overall construction is simple and can readily be made under mass production conditions.

DRAWINGS

Figure 2:
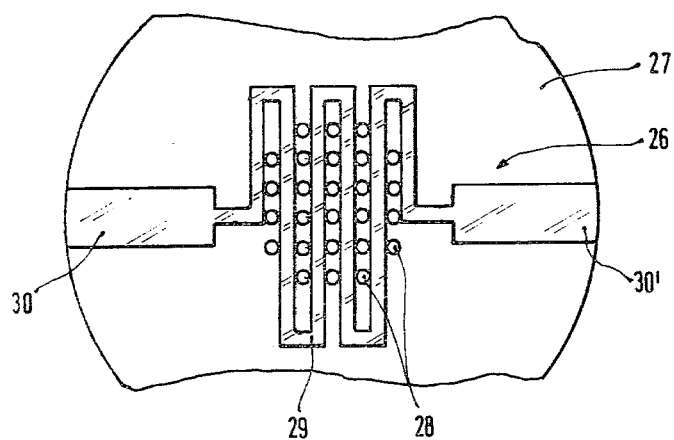

FIG. 1 is a fragmentary enlarged high schematic longitudinal sectional view through the sensing end of a sensor; and FIG. 2 is a cross-section through the sensor of FIG. 1 along line A-B.

The sensor illustrated in FIGS. 1 and 2 is a polarographic sensor 10 which determines oxygen concentration of gases by evaluation of the diffusion limiting current. The theoretical operation of a sensor is known, and described, for example, in U.S. Pat. No. 3,691,023 Ruka et al., and in the aforementioned U.S. Ser. No. 6,093 of Jan. 24, 1979, Dietz, assigned to the assignee of this application. The structure of the sensor remote from the sensing end can be in accordance with any well known construction, for example somewhat similar to the construction used in automotive-type spark plugs or, for example, as described in the referenced U.S. Pat. No. 4,155,827, Maurer et al.

The holding tube extending from the remainder of the housing portion of the sensor is a tube 11 made of ceramic, for example of aluminum oxide. It need not be gas impervious, but preferably is gas impervious. The tube 11 has an outer diameter of about 8 mm., a wall thickness of about 0.8 mm., and has an in-turned bottom 12 at the end thereof. The bottom 12 has a central opening 13 with a clear diameter of about 4 mm. The entire structure is circular in cross-section. At the inner wall 14 of the tube, an electrical conductor 15 is applied, extending over to the in-turned portion 12 of the bottom. Conductor 15 extends to the holding end portion of the housing for connection to a voltage source and to an evaluation circuit. The conductor 15 preferably is a conductive track made of platinum and applied by any well known thin film process, for example by vapor deposition, spray, or the like. A measuring electrode 16 is in surface contact with the conductive track 15. The measuring electrode 16 is porous, preferably consists of platinum, has a thickness of about 0.01 mm., and is applied to a plate-like solid electrolyte body 17, by any well known thin film technology, and, preferably, by printing. A thin gas impervious layer 18 is applied to the edge region of the solid electrolyte plate 17, the sensing electrode 16 extending thereover (see FIG. 1). The gas impervious layer 18 may be a thin glaze made of glass, leaving on the solid electrolyte body 17 a smaller region than the surface of the opening 13 in the bottom 12 of the housing tube 11. The solid electrolyte plate 17 preferably is made of stabilized zirconium dioxide, has a diameter of 5.6 mm., and a thickness of about 1 mm. Since the outer diameter of the solid electrolyte plate 17 is less than the inner diameter of the tube 11, a gap 19' will be left between the inside 19 of the holding tube 11 and the outer diameter of the solid electrolyte plate to permit expansion of the solid electrolyte plate under heating conditions. A layer 20 of magnesium spinel, of about ½ mm. thickness is applied to the sensing electrode 16. This layer extends into the opening 13 of the bottom 12 and is so made that it forms a predetermined diffusion or migration resistance to oxygen molecules, so that, upon application of a voltage between the electrode 16 and a counter electrode 21, the current flow will be an analog of the oxygen concentration, rather than merely representative of the presence or absence of oxygen. The diffusion layer preferably is applied by plasma spraying on the measuring electrode 16.

The counter electrode 21 is applied to the solid electrolyte plate 17 at its major surface opposite that on which electrode 16 is applied. Preferably, counter electrode 21, forming a reference electrode, is made of platinum, in accordance with any well known method, such as by vapor deposition, printing or the like. Like measuring electrode 16, it is gas pervious, and positioned opposite the measuring electrode 16. The solid electrolyte plate 17 with the measuring electrode 16, the gas impervious layer 18 at the edge thereof, the diffusion resistance layer 20 and counter electrode 21 form a common element which is easily mounted within the holding tube 11, by providing a single unitary sub assembly 22. The counter electrode 21 of the sub assembly 22 is engaged by the head 23 of the pressure contact formed by a bolt 24 which, in known manner, forms the second electrical connection to the measuring system. A detailed description is not necessary, see U.S. Pat. No. 4,155,817 Maurer et al, assigned to the assignee of this application, the disclosure of which is here by incorporated by reference. The bolt 24 is pressed by a force P against the end portion 12 of the tube 11. The force is resilient, as schematically indicated by spring P' and, at the other end, is supported by a suitable counter shoulder or the like, as schematically indicated by the counter surface which forms a part of, or is secured to the tube 11 of the sensor element 10. A suitable pressure contact at the contacting surface of head 23 is a silver plated or coated refractory material. The diameter of the pressure contact may be about 2 mm.

A heater 26 is located at the sensing end portion 25 of the bottom 12. The heater 26 has a heat storage plate 27 formed with gas penetration openings 28 through which the sensing gas can pass, and a film-like heater element 29. The heater element 29 is a meander-shaped conductive track applied to the heat storage plate 27. Preferably, the meander is so arranged that it is beneath the region of the opening 13 of the tube 11. The heating element preferably is of platinum and is applied to the diffusion or migration barrier 20 for the oxygen molecules. It is connected by two conductive tracks 30, 30' with the edge region of the heat storage plate 27. The diameter of the heat storage plate 27 corresponds approximately to the outer diameter of the holding tube 11. The conductive tracks 30, 30' leading to the heater element 29 thus can be engaged by in-turned conductive tracks 31, 31' which cover a portion of the looped-over side 25 of the bottom 12 of the tube 11, and which are continued as conductive tracks 32, 32' at the outside of the tube 11 to the connective region of the sensor—not shown—for subsequent connection to a suitable current 5. The heat storage plate 27 which, for example, is made of stabilized zirconium dioxide, or of aluminum oxide has a thickness of, for example, about 0.8 mm. It is adhered to the bottom 12 of the tube 11 by a suitable ceramic adhesive or ceramic cement.

The interior 14 of the tube 11 need not be sealed with respect to the sensing gas. The tube 11 may, even, be formed with a communication opening for the test gas, to communicate the inside with the outside. If, however, the surface of the counter electrode 21 is desired—for reasons of evaluation circuitry for example—to be exposed only to a reference gas, for example, oxygen in air, then the assembly 22 can be inserted in the holding tube 11 by using a suitable sealing element, or sealing material so that it is gas tight within the tube 11. The interior 14 of the tube 11 then can be exposed to a reference gas. The sealing mass which can be partly located within the gap 19' should preferably permit thermal expansion of the plate 17. A suitable material is: glass or glass ceramic.

The holding tube 11 preferably is made of an insulating electrical material, such as a ceramic. The holding tube 11, may, however, also be made of metal. If the holding tube 11 is made of metal, the conductive tracks 15 need not be used since the holding tube 11 may form the electrical connection to the electrode 16. On the other hand, however, the electrodes 32, 32' leading to the heater, and the respective portion 31, 31' extending over the bottom portion of the holding tube, as well as the contacting parts of the conductive tracks 30, 30' on the heat tube must be insulated, for example by a thin insulating layer of aluminum oxide or the like.

Various changes and modifications may be made within the scope of the inventive concept.

We claim:
1. Gas sensor construction, particularly to determine the oxygen content of combustion exhaust gases and especially exhaust gases from an internal combustion engine having
    an essentially tubular housing (11);
    a plate (17) of oxygen ion conductive solid electrolyte material;
    a first porous sensing electrode (16) applied to the plate at one major surface thereof;
    a second porous electrode (21) applied to the plate at the other major surface thereof and forming a counter electrode, said plate being positioned in the housing transversely with respect to the axis thereof;

and a gas permeable ceramic layer (26) closing the end of the tubular housing and positioned against said sensing electrode (17)

comprising, in accordance with the invention an in-turned end portion (12) formed on the tubular housing and forming a bottom, having a central opening (13) therethrough;

a gas impervious layer (18) positioned on the edge portion of the oxygen ion conductive solid electrolyte plate, the first sensing electrode (16) extending over the gas impervious layer;

electrical connections (15) extending longitudinally of the tubular housing and transversely thereof over the sensing electrode in the region where the electrode is located over said gas impervious layer (18);

resilient biased spring pressure (P') contact and support means (23,24) in engagement with said second counter electrode (21) on the other side of the plate, supported against said housing and pressing said plate and hence said electrode towards the end of the housing and establishing an electrical contact;

a heat storage plate (27) formed with gas passage openings (28) therethrough closing off the in turned end portion (12) of the housing (11);

a thin film heating element (29) located between the gas permeable ceramic layer (26) and the heat storage plate (27);

and electric connections (31, 31'; 32, 32') in electrical connection with said heating element and extending at least in part longitudinal of the housing.

2. Sensor construction according to claim 1, wherein the electrical connections (31, 31'; 32, 32') for the heating element (29) comprises conductive tracks located at the outside of the tubular housing and electrically insulated with respect to each other and with respect to the electrical connection means for said sensing electrode.

3. Sensor construction according to claim 1, wherein the essentially tubular housing comprises an insulating ceramic;

and wherein the electrical connection means to the sensing electrode (16) comprises a conductive track (15) formed on the inside of the ceramic tubular housing.

4. Sensor construction according to claim 3, wherein the tubular housing (11) comprises aluminum oxide.

5. Sensor construction according to claim 2 or 3 or 4, wherein the solid electrolyte plate has an outer diameter which is slightly less than the inner diameter of the tubular housing leaving a gap (19') to permit differential expansion of the plate and the tubular housing upon heating.

6. Sensor construction according to claim 1, wherein the solid electrolyte plate has an outer diameter which is slightly less than the inner diameter of the tubular housing leaving a gap (19') to permit differential expansion of the plate and the tubular housing upon heating.

7. Sensor construction according to claim 1, wherein said resiliently biased spring pressure contact and support means comprises an elongated bolt or pin (24) having a contact head (23) in engagement with said counter electrode (21) and extending essentially centrally of and longitudinally within the tubular housing.

8. Sensor construction according to claims 1 or 2 or 3 or 4 or 6 or 7 wherein the sensor is a polarographic sensor, and the gas permeable ceramic layer (26) comprises an oxygen migration or diffusion barrier.

* * * * *